US006808889B2

(12) United States Patent
Fitzpatrick et al.

(10) Patent No.: US 6,808,889 B2
(45) Date of Patent: Oct. 26, 2004

(54) METHOD AND DEVICE FOR DETECTION OF APO A, APO B AND THE RATIO THEREOF IN SALIVA

(75) Inventors: Judith Fitzpatrick, Tenafly, NJ (US); Regina B. Lenda, Wesley Hills, NY (US); Christopher L. Jones, Riverdale, NJ (US)

(73) Assignee: Serex, Inc., Maywood, NJ (US)

( * ) Notice: Subject to any disclaimer, the term of this patent is extended or adjusted under 35 U.S.C. 154(b) by 0 days.

(21) Appl. No.: 09/526,582

(22) Filed: Mar. 16, 2000

(65) Prior Publication Data

US 2003/0003501 A1 Jan. 2, 2003

Related U.S. Application Data

(60) Provisional application No. 60/124,562, filed on Mar. 16, 1999.

(51) Int. Cl.[7] .............................................. G01N 33/53
(52) U.S. Cl. ...................... 435/7.1; 435/7.92; 435/7.93; 435/7.94; 435/810; 436/518; 436/174; 436/808
(58) Field of Search .................... 435/5, 6, 7.1, 7.92, 435/7.93, 7.94, 808, 810, 970; 436/518, 524, 527, 528, 808, 174–179; 422/58

(56) References Cited

U.S. PATENT DOCUMENTS

| 5,112,758 A | * | 5/1992 | Fellman et al. ................. 436/8 |
| 5,137,808 A | * | 8/1992 | Ullman et al. ................ 435/7.9 |
| 5,162,237 A | * | 11/1992 | Messenger et al. .......... 436/523 |
| 5,384,264 A | * | 1/1995 | Chen et al. .................. 436/525 |
| 5,451,504 A | * | 9/1995 | Fitzpatrick et al. .......... 435/7.2 |
| 5,500,375 A | | 3/1996 | Lee-Own et al. |
| 5,559,041 A | * | 9/1996 | Kang et al. .................. 436/518 |
| 5,601,991 A | * | 2/1997 | Oberhardt ................... 435/7.91 |
| 5,602,040 A | * | 2/1997 | May et al. ................... 436/514 |
| 5,677,133 A | * | 10/1997 | Oberhardt .................... 435/7.1 |
| 5,710,009 A | | 1/1998 | Fitzpatrick et al. |
| 6,210,906 B1 | * | 4/2001 | Kundu et al. ................. 435/7.1 |
| 6,291,178 B1 | * | 9/2001 | Schneider ....................... 435/6 |

FOREIGN PATENT DOCUMENTS

| WO | WO 93/18067 | | 9/1993 | |
| WO | WO-94/12879 A1 | * | 6/1994 | ................. 422/68.1 |
| WO | WO 94/19690 A1 | | 9/1994 | |
| WO | WO 96/00903 | | 1/1996 | |
| WO | WO 98/06827 | | 2/1998 | |
| WO | WO 99/36784 A1 | | 7/1999 | |
| WO | WO 99/36785 A1 | | 7/1999 | |

OTHER PUBLICATIONS

Fisher et al., Salivary secretion of albumin type I insulin dependent diabetes, Diabetes Research and Clinical Practice, 11(2): 117–119 (Feb/1991) Abstract.*
Coppo et al., A Solid phase enzyme immunoassay for the measurement of urinary albumin and the detection of microalbuminurea, Journal of Diabetic Complications, 1(2): 58–60 (Mar–Apr/1987) Abstract.*

"Report of the Expert Panel on Blood Cholesterol Levels in Children and Adolescents," Pediatrics 89:525–584 (1992).
"Report of the National Cholesterol Education Program Expert Panel on Detection, Evaluation, and Treatment of High Blood Cholesterol in Adults," Arch. Intern. Med. 148:36–69 (1988).
"Report of the Working Group on Atherosclerosis of the National Heart and Lung and Blood Institute," 2 (Washington, D.C.: Government Printing Office. 1981) DHEW Publication No. (NIH) 82–2035).
"The Lipid Research Clinics Coronary Primary Prevention Trial Results: II", JAMA, 251:365–374 (1984).
ALAUPOVIC, "David Rubinstein Memorial Lecture: The Biochemical and Clinical Significance of the Interrelationship Between VeryLow Density and High Density Lipoproteins," Can. J. Biochem. 59:565–579 (1981).
ALAUPOVIC, et al., "Characterization of Potentially Atherogenic Triglyceride–rich Lipoprotein Particles," Klin. Wochenschr. 68:38–42 (1990).
ALAUPOVIC, et al., "Distribution of Lipoprotein Families in Major Density Classes of Normal Human Plasma Lipoproteins," Biochim. Biophys. Acta. 260:689–707 (1972).
ALAUPOVIC, et al., "Isolation and characterization of an apoA–II–containing lipoprotein (LP–A–II:B complex) from plasma very low density lipoproteins of patients with Tangler disease and type V hyperlipoproteinemia," J. Lipid Res. 32(1):9–19 (1991).
ARNTZENIUS, "Regression of Atherosclerosis—Benefit can be Expected from Low LDL–C and High HDL–C Levels," Acta. Cardiol. 46:431–438 (1991).
ASSMANN, et al., "The Hypertriglyceridemias: Risk and Management," Am. J. Cardiol, 68(3):1A–4A (1991).
ATMEH, et al., "Subpopulations of Apolipoprotein A–I in Human High–Density Lipoproteins, Their Metabolic Properties and Response to Drug Therapy," Biochem. Biophys. Acta. 751:175–188 (1983).
AVOGARDO, et al., "Are Apolipoproteins Better Discriminators than Lipids for Atherosclerosis?" Lancet 1:901–903 (1979).

(List continued on next page.)

Primary Examiner—Long V. Le
Assistant Examiner—Gary W. Counts
(74) Attorney, Agent, or Firm—Patrea L. Pabst, Esq.

(57) ABSTRACT

A method has been developed to detect the levels of apolipoproteins A-1 and B in saliva, which is correlated with the levels of HDL and LDL in serum, respectively. In unstimulated saliva, the ration of Apo A to Apo B is correlated with the ration of HDL to LDL in serum. Albumin can be used to normalize the sample for dilution. The high degree of correlation in combination with a simple, quick test that can be performed at the site of collection provides a cost effective, patient friendly means to monitor an individual's risk of heart disease. In the preferred embodiment, saliva production is stimulated by means such as breath mint or tart solution (such as lemon) and the effect of dilution controlled by reference to albumin.

22 Claims, 6 Drawing Sheets-

OTHER PUBLICATIONS

BARTH, et al., "Progression and Regression of Atherosclerosis, What Roles for LDL–Cholesterol and HDL–Cholesterol: A Perspective," *Eur. Heart J.* 12:952–957 (1991).

BLANKENHORN, et al., "Prediction of Angiographic Change in Nature Human Coronary Arteries and Aortocoronary Bypass Grafts," *Circulation* 81(2):479–476 (1990).

BRONSLAW, et al., "Lipids of Saliva and Salivary Concretions," in *Human Saliva: Clinical Chemistry and Microbiology,* vol. II, pp. 121–145, CRC Press Inc. 1989.

CARDIN, et al., "Degradation of Apolipoprotein B–100 of Human Plasma Low Density Lipoproteins by Tissue and Plasma Kallikreins," *J. Biol. Chem.* 259(13):8522–8528 (1984).

CLACKSON, et al., "Making antibody fragments using phage display libraries," *Nature* 352: 624–628 (1991).

CURRY, et al., "Determination of Apolipoprotein A and Its Constitutive A–I and A–II Polypeptides by Separate Electroimmunoassays," *Clin. Chem.* 22(3):315–322 (1976).

CURRY, et al., "Determination of Human Apolipoprotein E by Electroimmunoassay," *Biochem. Biophys. Acta.* 439:413–425 (1976).

CURRY, et al., "Electroimmunoassay, Radioimunoassay, and Radial Immunodiffusion Assay Evaluated for Quantification of Human Apolipoprotein B," *Clin. Chem.* 24(2):280–286 (1978).

CURRY, et al., "Quantitative Determination of Human Apolipoprotein C–III by Electroimmunoassay," *Biochim. Biophys. Acta.* 617:503–513 (1980).

CWIRLA, et al., "Peptides on phage:A vast library of peptides for identifying ligands," *Proc. Natl. Acad. Sci. USA* 87:6378–6382 (1990).

DIEM, et al., *Scientific Tables,* p. 643, (Ciba–Geigy Pharmaceuticals, 1970).

FRIEDEWALD, et al., "Estimation of the Concentration of Low–Density Lipoprotein Cholesterol in Plasma, Without Use of the Preparative Ultracentrifuge," *Clin. Chem.* 18(6):499–502 (1972).

FRUDCHART & AILHAUD, "Apolipoprotein A Containing Lipoprotein Particles: Physiological Role, Quantification, and Clinical Significance," *Clin. Chem.* 38(6):793–797 (1992).

FRUDCHART, et al., "Simultaneous measurement of plasma apolipoproteins A–1 and B by electroimmunoassays," *Clin. Chem.* 28(1):59–62 (1982).

GALEANO, et al., "Apoprotein B structure and receptor recognition of triglyceride–rich low density lipoprotein (LDL) is modified in small LDL but not in triglyceride–rich LDL of normal size," *J. Biol. Chem.* 269(1):511–519 (1994).

GALFRE, et al., "Preparation of Monoclonal Antibodies: Strategies and Procedures," *Methods Enzymol.* 73:3–46 (1981).

GLENNER, "Formazans and Tetrazolium Salts," *H.J. Conn's Biological Stains,* pp. 225–235, The Williams and Wilkins Company, 1990.

GODING, "Monoclonal Antibodies: Principles and Practice," pp. 56–97, Academic Press, Inc.:New York (1983).

GOHLKE, "Influence of the LDS–/HDL–Cholesterol Rate on Progression and Regression of Atherosclerotic Lesions. A Review of Controlled Angiographic Intervention Trials," *Wien Klin. Wochenschr.* 104(11):309–313 (1992).

GORDON, et al., "High density lipoprotein as a protective factor against coronary heart disease. The Framingham Study," *Am. J. Med.* 62(5):707–714 (1977).

HAECKEL, "Factors influencing the saliva/plasma resin of drugs," *Ann. N. Y. Acad. Sci.* 694:128–142 (1993).

HARDUIN, et al., "Modulation of the expression of human LDL–Apo B–100 epitopes by lipids and apolipoproteins," *Arterioscler. Thromb.* 13(4):529–535 (1993).

HOLLINGER, et al., "Databodies: Small bivalent and Bispecific Antibody Fragments," *Proc. Natl. Acad. Sci. USA* 90:6444–6448 (1993).

HODGENBOOM, et al., "Multi–Subunit Proteins on the Surface of Filamentous Phage: Methodologies for Displaying Antibody (Fab) Heavy and Light Chains," *Nucl. Acids Res.* 19(15):4133–4137 (1991).

ITO, et al., "Development of an Artificial Antibody System with Multiple Valency Using an Fv Fragment Fused to a Fragment of Protein A," *J. Biol. Chem.* 268(27):20668–20675 (1993).

KANE, "Characterization of apolipoprotein B–containing lipoproteins," *Methods Enzymol.* 129:123–129 (1986).

KASHYAP, et al., "Radioimmunoassay of human apolipoprotein CII. A study in normal and hypertriglyceridemic subjects," *J. Clin. Invest.* 60(1):171–180 (1977).

KEIDAR, et al., "A high carbohydrate–fat free diet alters the proportion of heparin–bound VLDL in plasma and the expression of VLDL–spoB–100 epitopes," *Metabolism* 39(3):281–288 (1990).

KWITEROVICH, et al., "Comparison of the Plasma Levels of Apolipoprotein B and A–1, and Other Risk Factors in Men and Women with Premature Coronary Artery Disease," *Am. J. Cardiol.* 69:1015–1021 (1992).

KWITEROVICH, et al., "Prevalence of Hyperapobetalipoproteinemia and Other Lipoprotein Phenotypes in Men (Aged ≦50 Years) and Women (≦60 Years) With Coronary Artery Diseases," *Am. J. Cardiol.* 71:631–639 (1993).

LA BELLE, et al., "Increased immunoreactivity of apolipoprotein B epitopes during prolonged storage of low density lipoproteins," *Clin. Chim. Acta.* 191(3):153–160 (1990).

LARSSON, ET AL., "Lipids in Human Saliva," *Arch. Oral Biol.* 41(1):105–110 (1996).

LEE, et al., "Properties of Apolipoprotein B in Urea and in Aqueous Buffers—The Use of Glutathione and Nitrogen in Its Solubilization," *Biochim. Biophys. Acta.* 666:133–146 (1981).

LOCHNER, "Gas chromatographic—Mass spectrometric analysis of violatile constituents in saliva (profiles)," *Dissertation Abstract International* Vol. 46, #5B (1985).

LOPES–VIRELLA, et al., "Cholesterol Determination in High–Density Lipoproteins Separated by Three Different Methods," *Clin. Chem.* 23:(5):882–884 (1977).

LOWMAN, et al., "Selecting High–Affinity Binding Proteins by Monovalent Phage Display," *Biochemistry* 30:10832–10838 (1991).

MACIEJKO, et al., "Apolipoprotein A–I as a Marker of Angiographically Assessed Coronary–Artery Disease," *N. Engl. J. Med.* 309(7):385–389 (1983).

MANDEL & EISENSTEIN, "Lipids in human salivary secretions and salivary calculus," *Arch. Oral Biol.* 14(2):231–233 (1969).

MARCEL, et al., "Expression of human apolipoprotein A–I epitopes in high density lipoproteins and in serum," *J. Lipid Res.* 28(7):768–777 (1987).

MCGILL, et al., "Relationship of Blood Cholesterol and Apoprotein B Levels to Angiographically Defined Coronary Artery Disease in Young Males," *Coron. Artery Dis.* 4(3):261–270 (1993).

MEZES, "Construction and Biodistribution Studies of Multivalent Single–Chain Antibodies," *Construction and Biodistribution Studies of Multivalent Single–Chain Antibodies, The Fourth Annual IBC International Conference on Antibody Engineering,* Dec., 1993, Coronado, Calif.

MILLER & MILLER, "Plasma–high–density–lipoprotein concentration and development of ischaemic heart disease" *Lancet* 1(7897):16–19 (1975).

MILLER, et al., "The Tromso heart–study. High–density lipoprotein and coronary heart–disease: a prospective case–control study," *Lancet* 1(8019):965–969 (1977).

MILINE, et al., "The use of monoclonal antibodies to localize the low density lipoprotein receptor–binding domain of apolipoprotein B," *J. Biol. Chem.* 264(33):19754–19760 (1989).

MULDER, et al., "An Evaluation of Three Commercial Methods for the Determination of LDL–Cholesterol," *Clin. Chim. Acta.* 143:29–35 (1984).

OLOFSSON, et al., "Isolation and Partial Characterization of a Polypeptide Belonging to Apolipoprotein B from Low–Density Lipoproteins of Human Plasma," *Biochemistry* 19:1059–1064 (1980).

ORTOLA, et al., "Biological Variation Data Applied to the Selection of Serum Lipid Ratios used as Risk Markers of Coronary heart Disease," *Clin. Chem.* 38(1):56–59 (1992).

OSBORNE & BREWER, "The plasma lipoproteins," *Adv. Protein Chem.* 31:253–337 (1977).

PARHAM, "Handbook of Experimental Immunology, Vol. 1: Immunochemistry," (Weir, D. M., Editor), Blackwell Scientific Publications: Oxford, 1986.

PARMLEY, et al., "Filamentous Fusion Phage Cloning Vectors for the Study of Epitopes and Design of Vaccines," *Adv. Exp. Med. Biol.* 251:215–218 (1989).

PUCHOIS, et al., "Apolipoprotein A–I Containing Lipoproteins in Coronary Artery Disease," *Atheroschlerosis* 68:35–40 (1987).

RABINOWITZ & SHANNON, "Lipid changes in human male parotid saliva by stimulation," *Arch. Oral Biol.* 20(7):403–406 (1975).

RIFAI, et al., "Introduction," *Atherosclerosis* 108(Suppl):S1–S2 (1994).

SAVAGE, et al., "Avidin–Biotin Chemistry: A Hardbook," Pierce Chemical Company, Rockford, Ill. (1992).

SLOMIANY, et al., "Association of lipids with proteins and glycoproteins in hyman saliva," *J. Dent. Res.* 62(1):24–27 (1983).

SLOMIANY, et al., "Lipid composition of human parotid and submandibular saliva from caries–resistant and caries–susceptible adults," *Arch. Oral. Biol.* 27(10):803–808 (1982).

SMITH, et al., "The plasma lipoproteins: structure and metabolism," *Annu. Rev. Biochem.* 47:751–757 (1978).

SNIDERMAN, et al., Association of Coronary Atherosclerosis with Hyperapobetalipoproteinemia [Increased Protein but Normal Cholesterol Levels in Human Palsma Low Density ($\beta$) Lipoproteins], *Proc. Natl. Acad. Sci. USA* 77(1):604–608 (1980).

SOCORRO & CAMEJO, "Preparation and Properties of Soluble, Immunoreactive ApoLDL," *J. Lipid Res.* 20:631–638 (1979).

STEIN, et al., "Lipids, Lipoproteins, and Apolipoprotein," in *Tietz Textbook of Clinical Chemistry,* pp. 1002–1093, W.B. Saunders:Philadelphia, 1994.

TORNVALL, et al., "Relation of Plasma Levels and Composition of Apolipoprotein B–Containing Lipoproteins to Angiographically Defined Coronary Artery Disease in Young Patients with Myocardial Infarction," *Circulation* 88:2180–2189 (1993).

TOUCHSTONE, et al., "Quantitation of Cholesterol in Biological Fluids in TLC with Densitometry" *Adv. Thin Layer Chromatogra.,* Proc. Bienn. Symp. Meeting Date 1980, pp. 219–227, Wiley & Sons 2nd ed., 1982.

WARNICK, et al., "Dextran Sulfate–$Mg^{2+}$ Precipitation Procedure for Quantitation of High–Density–Lipoprotein Cholesterol," *Clin. Chem.* 28(6):1379–1388 (1982).

WEEKS, et al., "Two–site immunochemiluminometric assay for human alpha 1–fetoprotein," *Clin. Chem.* 29(8):1480–1483 (1983).

WOLLENWEBER, et al., "Comparative Serum Lipoprotein Analysis by Polyacrylamide Disc Gel and Agarose Gel Electrophoresis," *Clin. Chim. Acta.* 29:411–420 (1970).

WOOD, et al., "Heterogeneous fluoroimmunoassay" In *Principles and Practice of Immunoassay,* pp. 365–392, Stockton Press:New York, 1991.

\* cited by examiner

METHOD AND DEVICE FOR DETECTION OF APO A, APO B AND THE RATIO THEREOF IN SALIVA

The present invention is generally in the field of assays for apoliproteins in saliva.

This application claims priority to U.S. Ser. No. 60/124,562 filed Mar. 16, 1999.

BACKGROUND OF THE INVENTION

Coronary artery disease (CAD) is the leading cause of morbidity and mortality in most developed countries. Numerous markers and tests for identifying individuals at risk are available, among them blood tests for lipid markers such as total cholesterol and cholesterol bound to various circulating proteins. Based on the outcome of such testing, appropriate prophylactic or therapeutic measures including dietary modification and exercise can be initiated to forestall or reverse progression to more severe CAD.

Plasma lipoproteins are carriers of lipids from the sites of synthesis and absorption to the sites of storage and/or utilization. Lipoproteins are spherical particles with triglycerides and cholesterol esters in their core and a layer of phospholipids, nonesterified cholesterol and apolipoproteins on the surface. They are categorized into five major classes based on their hydrated density as very large, triglyceride-rich particles known as chylomicrons (less than 0.95 g/ml), very low density lipoproteins (VLDL, 0.95 to 1.006 g/ml), intermediate-density lipoproteins (IDL, 1.006 to 1.019 g/ml), low-density lipoproteins (LDL, 1.019 to 1.063 g/ml) and, high-density lipoproteins (HDL, 1.063 to 1.210 g/ml). (Osborne and Brewer, *Adv. Prot. Chem.* 31:253–337 (1977); Smith, L. C. et al. *Ann Rev. Biochem.*, 47:751–777 (1978)).

Apolipoproteins are protein components of lipoproteins with three major functions: (1) maintaining the stability of lipoprotein particles, (2) acting as cofactors for enzymes that act on lipoproteins, and (3) removing lipoproteins from circulation by receptor-mediated mechanisms. The four groups of apolipoproteins are apolipoproteins A (Apo A), B (Apo B), C (Apo C) and E (Apo E). Each of the three groups A, B and C consists of two or more distinct proteins. These are for Apo A: Apo A-I, Apo A-II, and Apo A-IV, for Apo B: Apo B-100 and Apo B-48; and for Apo C: Apo C-I, Apo C-II and Apo C-III. Apo E includes several isoforms. Each class of lipoproteins includes a variety of apolipoproteins in differing proportions with the exception of LDL, which contains Apo B-100 as the sole apolipoprotein. Apo A-I and Apo A-II constitute approximately 90 percent of the protein moiety of HDL whereas Apo C and Apo E are present in various proportions in chylomicrons, VLDL, IDL and HDL. Apo B-100 is present in LDL, VLDL and IDL. Apo B-48 resides only in chylornicrons and so called chylomicron remnants (Kane, J. P., *Method. Enzymol.* 129:123–129 (1986)).

Total plasma or serum cholesterol (C) has traditionally been the primary screening and indicator of CAD, but the emphasis has recently shifted to serum lipoprotein profiles including HDL, LDL, VLDL, lipoprotein A and particularly to the LDL/HDL or Total C/HDL ratios which have shown better correlations with incidence and severity of CAD. In contrast to the atherogenic potential of LDL, VLDL and VLDL remnants, HDL are inversely correlated with CHD, so that individuals with low concentrations of HDL-C have an increased incidence of CHD (Gordon, T. et al., *Am. J. Med.*, 62:707–714 (1977); Miller, N. E. et al., *Lancet*, 1:965–968 (1977); Miller, G. J. and Miller, N. E., *Lancet*, 1:16–19 (1975)).

A large number of manual and automated methods are available for screening and monitoring of these markers. All of these tests, however, require either venous blood drawn by syringe or, in some cases, capillary blood obtained by needle prick. Both methods are invasive and unpleasant to many individuals and are best performed by trained professional personnel, preferably in doctor's office, to minimize erroneous results. Handling and disposal of blood products also involves potential hazards from infectious agents and pathogens.

It is thus highly desirable to provide safer alternative specimens not requiring invasive procedures. Furthermore, the ideal analytical method or device should provide rapid and reliable results for point of collection ("POC") diagnosis at low cost.

Most analytes that appear in serum also appear in saliva, but at levels that are a fraction of their level in serum. The transport of an analyte into saliva can be by intracellular (diffusion or passive transport) or extracellular (active transport) transport. Materials that are lipid soluble enter saliva by diffusion through cellular compartments. Haekcel, Ann. N.Y. Acad. Sci. 694, 128–142 (1993).

Saliva has not been exploited as a diagnostic fluid because of the many problems associated with adapting it to assay form. For example, it is difficult to collect sufficient sample: Most tests require collection of at least 1 ml of saliva because there is considerable loss during filtration and handling. This requires an average of 3–5 minutes of salivation, which most people are not willing to do. The average flow rate for 95% of young men is 0.35–0.38 ml/min. (K. Diem, et al (ed) Scientific Tables (Ciba-Geigy Pharmaceuticals 1970) p. 643. Moreover, the handling of saliva samples to prepare them for assay is both tedious and unpleasant. Saliva generally has to be filtered to remove the mucopolysaccharides and allow flow and handling. Available collection devices utilize cotton pads to absorb saliva in the mouth. The pad thus acts to collect and process the saliva, preparing it for assay. The pad is then placed in a volume of fluid containing preservatives and shipped to the laboratory for analysis. The preservative fluid prevents quantitation by making it impossible to know how much saliva, if any, was collected and added to the preservative. When the device reaches the lab the technicians must remove the pad and mucopolysaccharides either by centrifugation or filtration. This is a time consuming and unpleasant job. The small amount of saliva sample and low level of analyte in saliva usually means that the saliva sample cannot be analyzed by an autoanalyzer, but must be assayed in a high sensitivity Elisa or RIA, both of which are labor-intensive tests.

Many studies of saliva have shown that the levels of analytes vary with the secreting gland and the method of collection (e.g. stimulated flow versus normal flow). For reviews see Saliva as a Diagnostic Fluid (D. Malmud and L. Tobak, Eds., Ann. N.Y. Acad. Sci. Vol. 694 D (1993) and J. O. Tenuvuo (ed) Human Saliva: Clinical Chemistry and Microbiology (CRC Press Inc. 1989) vol. I and II). Thus, one presumes that the significant variations in lipid levels reported in saliva are in large part due to collection method. Levels of cholesterol are also low, with cholesterol levels of about 1/400 and about 1/50 of that seen in serum. Bronislaw, et al., "Lipids of Saliva and Salivary Concretions," in Human Saliva: Clinical Chemistry and Microbiology (CRC Press Inc. 1989) vol. II, 121–145). Thus the level in an individual sample is too low for conventional serum assays in the routine assay of lipids in saliva, therefore either requiring the use of sensitive immunoassays or a larger quantity of saliva. J. C Touchstone, et al., "Quantitation of Cholesterol in Biological." in Adv. Thin Layer Chromatogr., Proc. Bienn. Symp. Meeting Date 1980, (Wiley & Sons $2^{nd}$ ed. 1982) measured total cholesterol and lipids. Moreover, there is a variation in levels depending on the time of day and from day to day (less than 8%), with levels highest in morning specimens and lower throughout the day, suggesting that saliva testing of cholesterol be done at the same time of the day.

Another problem with using saliva is that saliva is heavily contaminated with the oral flora. Available collection devices provide high levels of preservatives to retard growth of bacteria but, unless the sample is carefully preserved (e.g. by freezing), samples often become putrefied and laboratory technicians avoid processing saliva. Furthermore, high levels of preservatives can interfere in many assays. Saliva also contains many proteins and enzymes of both salivary and bacterial origins. Over time these enzymes and proteins can interact with the analytes of interest and make the assay of some analytes impossible. Thus, as a rule, stored samples cannot be expected to yield accurate results unless the storage additives and conditions are optimized for the analyte.

The literature reports that, while cholesterol is present in saliva, the levels vary greatly. For example, 5.6 mg/L average was reported by B. Larsson, et al, "Lipids in Human Saliva" in Archs. Oral. Biol. 41(1), 105–110 (1996); 15 mg/L average was reported for both the parotid and submandibular glands saliva output by Slomiany, et al, J. Dent. Res. 61(1), 24–27 (1983); and 69 mg/L was reported by Rabinowitz, et al, Arch. Oral. Biol. 20(7), 403–406 (1975).

As noted above, the ratio of LDL:HDL ratio is an established predictor of the risk of coronary artery disease. The recent NCEP guidelines call for use of ratio rather than total cholesterol. It has been reported that men with acceptable total cholesterol levels but ratios of LDL:HDL above 3.5 were 50% more likely to have coronary heart disease than their counterparts with lower ratios. It is a matter of time before total cholesterol is supplanted by ratios.

Immunoassays for lipoproteins associated with HDL and LDL have been shown to correlate with the measurement of cholesterol ratios in these two fractions. N. Rifai, et al (ed) Laboratory Measurement of Lipids, Lipoproteins and Apolipoproteins (AACC Press 1994) p. 114. The results correlate with the methods where HDL and LDL fractions are physically separated and measured (Laboratory Measurement of Lipids, Lipoproteins and Apolipoproteins. 1994. N. Rifai and R. Warnick Eds. AACC Press.)

It is not known if the proteins with which salivary cholesterol is associated are the same as those in serum, i.e. ApoAI and ApoBII. It is clear from all studies (Belmont) (Mandel, et al, Arch. Oral. Biol. 14(2), 231–233 (1969)) that salivary lipids are secreted by the glands in conjunction with lipoproteins(s). Slomiany et al also demonstrated that the lipids in saliva are associated with proteins. There is no published literature, however, on the origin of the lipids or their physical state in saliva" (Larsson et al). Thus, from the early literature, it is not clear whether the salivary lipids are synthesized de novo in the salivary glands or are derived from serum; and, if they are serum derived, if the salivary apolipoproteins are the same as the apolipoproteins associated with LDL and HDL in serum. There are other salivary glycoproteins also associated with the lipid. It is not clear from the literature whether the structure of the lipid particles in saliva is the same as those in serum and whether the conformation of the apolipoproteins is the same in saliva as in serum. Rabinowitz suggests that lipids secreted by the glands are secreted associated with lipoprotein. He demonstrated that the lipid levels drop in stimulated saliva but retain the same ratio to one another. Larsson reports that salivary lipoprotein fractions are of much higher density than serum lipoproteins and concludes that the salivary lipids are differently aggregated.

Various studies have indicated that the saliva levels of cholesterol show a gross correlation with serum cholesterol levels (Lochner, A. Dissertation Abstract International (1985) Vol. 46, #5B). It has also been observed that there is a positive correlation between persons with hypercholesteremia. Slorniany, et al, Arch. Oral. Biol. 27(10), 803–808 (1982) and Murty, et al, RCS Med. Sci. 10(5), 359 (1982). The paucity of studies correlating serum and saliva cholesterol may be due to the fact that the available methods for assaying cholesterol and thus correlating serum and saliva have been too insensitive. The enzymic and chromatographic methods of detecting cholesterol rely on high levels not available in saliva. Thus, these methods require large amounts of saliva and studies on lipids have generally been done on pools. Measurement of cholesterol in saliva is further complicated because saliva contains high amounts of peroxidase, an enzyme component of some cholesterol assays.

It is therefore an object of the present invention to provide a non-invasive, non-instrumental, accurate, simple and cost-effective means for determination of a marker for CAD, HDL, LDL, and/or the ratio of LDL:HDL.

SUMMARY OF THE INVENTION

A method and kit has been developed to detect the levels of apolipoproteins A-1 and B in saliva, which is correlated with the levels of HDL and LDL in serum, respectively. In unstimulated saliva, the ratio of Apo A to Apo B is correlated with the ratio of HDL to LDL in serum. In stimulated saliva the levels of Apo B normalized to albumin correlate with both serum Apo B and serum LDL. The high degree of correlation in combination with a simple, quick test that can be performed at the site of collection provides a cost effective, patient friendly means to monitor an individual's risk of heart disease. In the preferred embodiment, saliva production is stimulated by means such as breath mint or tart solution (such as lemon) and the effect of dilution controlled by reference to albumin. In the most preferred embodiment, the assay is an immunoassay performed using the Serex laminated strip format as described in U.S. Pat. Nos. 5,710,009, 5,500,375, and 5,451,504. These strips are advantageous since they serve as the collection and assay device, greatly simplifying handling, as the sample is applied directly to the strip test and processed as an integral part of the analytical procedure. This method requires less than 200 microliters, which should be available in the average person's mouth at any time. Additional saliva production can be obtained, however, using breath mints or a tart juice such as lemon juice. The assay of saliva at POC will eliminates the need for preservatives to store the sample and entirely avoids the problem with contamination by oral flora, since the assay can be completed within 10 minutes of saliva collection.

DETAILED DESCRIPTION OF THE INVENTION

It has now been demonstrated that ApoA and ApoB are both present in saliva, but that these proteins are not detectable by electrophoresis or immunoassay except in very fresh samples, presumably due to degradation of the lipoproteins by saliva enzymes or bacteria or both. This explains why other studies have not observed these proteins; since they detected cholesterol by enzymic methods, and in the time required for this the proteins were degraded.

I. Reagents for Detection of Apolipoproteins

Antibodies are known in the literature and available from commercial sources and from the ATCC.

Antibodies to Apo B

Antibodies to Pan B $D_6$ MAb is an antibody with equal binding and high affinity for all Apo B-containing lipoproteins in human plasma, as described by Koren, E. et al., *Biochim. Biophys. Acta*, 876:91–100 (1986); Koren, E. et al., *Biochim. Biophys. Acta*, 876:101–107 (1986), specifically including Apo B-48 and Apo B-100. $D_6$ binds to an epitope localized at the amino terminal half of Apo B and recognizes both B-48 and B-100.

Antibodies to Apo B-100

Conventional ways of producing Monoclonal antibodies to Apo B-100 include immunization of mice with LDL. This approach is convenient because it is relatively simple to isolate LDL. However, Monoclonal antibodies produced using LDL as an immunogen tend to be sensitive to conformational changes of Apo B-100 caused by variations in the lipid composition of LDL particles. For example, Apo B-100 epitopes are less reactive with a number of anti-Apo B Monoclonal antibodies due to the presence of various amounts of triglycerides (Keidar, S. et al., *Metabolism*, 39: 281–288 (1990); Galeano, N. F. et al., *J. Biol, Chem.*, 269:511–519 (1994); Harduin, P. et al., *Arterioscl. Thromb*, 13: 529–535 (1993)).

PCT PCT/US95/08331 *"Antibodies to Lipoproteins and Apolipoproteins and Methods of Use Thereof"* by Oklahoma Medical Research Foundation describes antibodies that provide selective recognition of LDL and high and invariable reactivity with LDL particles, irrespective of possible variations in their lipid composition and/or conformation, that is, an antibody which recognizes a stable, conformation-independent epitope which is uninfluenced by the lipid content and which is equally expressed in all LDL particles, but inaccessible in VLDL and chylomicrons. $HB_3cB_3$ binds to the epitope near the T2 carboxy terminal region of B-100, exclusively, and does not recognize B-48. The epitope recognized by $HB_3cB_3$ may be conformationally changed or masked by lipids and/or other apolipoproteins present in VLDL. Chylomicrons are not recognized by $HB_3cB_3$ because they lack Apo B-100. The $HB_3cB_3$ antibody and LDL-binding fragments derived therefrom, can be used as an LDL-specific binding molecule in all of the compositions and methods described herein because of its specificity for LDL and lack of cross-reactivity with other lipoproteins.

Two other LDL specific Monoclonal antibodies are described by Milne, R. et al., *J. Biol Chem.*, 264:19754–19760 (1989); and WO 93/18067 by La Belle, et al. and La Belle, M. et al., *Clin. Chim. Acta*, 191:153–160 (1990) (8A2.1 and 4B5.6).

Antibodies to Apo A-I

Two antibodies to Apo A-I are also described in PCT PCT/US95/08331 by OMRF which both bind to HDL with a high affinity and show negligible reactivity with any other lipoprotein density class. The two anti-Apo A-I Monoclonal antibodies, $AIbD_5$ and $AIbE_2$, bind to sterically distant epitopes since they do not compete with each other in their binding to either delipidized and purified Apo A-I or intact HDL particles. Both Monoclonal antibodies to Apo A-I bind with high affinity to delipidized Apo A-I and to HDL and show negligible or no binding to LDL, VLDL, chylomicrons and Apos A-II, C-III and E Antibodies to Apo A-II A monoclonal antibody to Apo A-II which binds with high affinity to HDL and is capable of removing all the HDL particles containing Apo A-II (LP-A-I:A-II particles) from plasma or serum, leaving the HDL particles without Apo A-II (LP-A-I particles) intact, $CdB_5$, is described by Koren, E. et al., *Arteriosclerosis*, 6:521a (1986); Alaupovic, P. et al., *J. Lpid Res.*, 32:9–19 (1991).

Antibodies to Apo C-III

An MAb to Apo C-III, $XbA_3$, which is useful in quantification of VLDL particles is described by Koren, E. et al., *Atherosclerosis*, 95:157–170 (1992).

Antibodies to Apo E

Two Monoclonal antibodies to Apo E are described by Koren, E. et al., *Atherosclerosis*, 95:157–170 (1992). One of them, $EfB_1$, binds preferably to Apo E associated with VLDL which are precipitated by heparin whereas the other ($EfD_3$) binds predominantly to Apo E in HDL which are not precipitated by heparin treatment of a sample.

II. Sample Preparation

In a preferred embodiment, saliva is collected, filtered through cotton or a similar pore size filter to remove mucopolysaccharides, and kept chilled to 4° C. until assayed. Preferably the sample is assayed within three hours of collection. Preservatives and protease or other enzyme inhibitors can be added to the sample.

III. Simultaneous Sample Collection, Preparation and Assay

In an alternative embodiment, an integrated collection and assay device can be used. As described in PCT PCT/US98/16256 *"Integrated Collection and Assay Device for Saliva and Blood"* by Serex, Inc., this device can include a fluid collector, a processing and metering pad and/or filter, and one or more assay strips. The fluid collector can be adapted for collection of saliva or blood. The assay strips can be any type presently used. Nitrocellulose is a preferred material. Preferably, the assay strips are laminated dipsticks such as described in U.S. Pat. No. 5,500,375.

In a preferred embodiment, this device includes holder having a stem portion and a funnel portion. In one embodiment, the holder can be a double sheet of plastic that is laminated together at the stem portion. For example, the holder can be made of polyethylene or another clear, flexible plastic. The funnel portion is sealed on the edges to form lateral seals that extend down the stem portion. Thus, an open top collection "funnel" is formed in the funnel portion, which is in fluid communication with the stem portion. At the neck of the device, or the juncture of the funnel portion and stem portion, is the processing and metering pad. The pad is preferably an absorbent pad or sponge which serves to filter oral debris and mucopolysaccharides from the sample. It can be formed of any suitable material, preferably of a fibrous nature, most preferably a material such as a cellulose or cellulose derivative. In some embodiments, the material may be charged or contain substances which effect separations or passage through the filter. For example, the pad may also contain buffers and reagents such as dissociating or mucolytic agents and surfactants which may be required. The pad further serves to meter the amount of sample which is transferred to the assay strip. This is accomplished by selection of the size, shape, porosity and composition of the pad, which can be adjusted as necessary to optimize separation and metering of sample volume.

The device includes one or more assay strips. These may be of the same or different materials, providing for measurement of multiple analytes in the sample. The assay strip extends from the pad into the stem portion. The assay strip includes a carrier which supports a membrane which is in liquid communication with the pad. The assay strip can be any chromatographic assay strip but is preferably designed as described in U.S. Pat. Nos. 5,500,375 and 5,710,009. In the most preferred embodiment, the membrane is a nitrocellulose strip which includes a sample application region adjacent to the processing or metering pad. The membrane further includes a mobilization zone having immobilized thereupon mobilizable labelled reagent, for example. The membrane also includes one or more trap zones. Three contain various reagents for capturing unreacted analyte or labelled analyte, for example, depending upon the design of the assay. In this preferred embodiment, the membrane further includes one or more detection zones which may be the same as one or more of the trap zones. The section of the holder overlying the detection zones is preferably clear so that the results of the assay can be read.

IV. Other Immunoassays

The apolipoproteins in the saliva can be measured using any of a number of different assays, including ELISA and automated immunoturbidimetric assays, as well as dipsticks made using conventional technology.

Elisa

In ELISA, sample is placed in separate wells in microtiter plates and allowed to adsorb to the wall of the wells. The wells are then treated with a blocking agent, such as bovine serum albumin or nonfat milk proteins, to cover areas in the wells not bound by antigen. Antibody is then added in an appropriate buffer to the well, in one or more concentrations and the microtiter plate incubated under conditions adequate to allow the antibody to bind the antigen adsorbed on the wall of each well. The presence of antibody bound to antigen (i.e., Apo A1, Apo B, etc.) in a well can then be detected using a standard enzyme-conjugated anti-antibody which will bind antibody that has bound to apolipoprotein in the well. Wells in which antibody is bound to antigen are then identified by adding a chromogenic substrate for the enzyme conjugated to the anti-antibody and color production detected by an optical device such as an ELISA plate reader.

Other detection systems can also be used, for example, a biotin-streptavidin system. In this system, one of the antibodies (either the antibody immunoreactive with the apolipoprotein or the antibody immunoreactive with the specific antibody) is biotinylated. The nonbiotinylated antibody are incubated with wells coated with the apolipoprotein or lipoprotein antigen. Quantity of biotinylated antibody bound to the coated antigen is determined using a streptavidin-peroxidase conjugate and a chromogenic substrate.

Antibodies can alternatively be labeled with any of a number of fluorescent compounds such as fluorescein isothiocyanate, europium, lucifer yellow, rhodamine B isothiocyanate (Wood, P. In: *Principles and Practice of Immunoasay*, Stockton Press, New York, pages 365–392 (1991)) for use in immunoassays. In conjunction with the known techniques for separation of antibody-antigen complexes, these fluorophores can be used to quantify apolipoprotein. The same applies to chemiluminescent immunoassay in which case antibody or apolipoprotein can be labeled with isoluminol or acridinium esters (Krodel, E. et al., In: *Bioluminescence and Chemiluminescence: Current Status*. John Wiley and Sons Inc. New York, pp 107–110 (1991); Weeks, I. et al., *Clin. Chem.* 29:1480–1483 (1983)). Radioimmunoassay (Kashyap, M. L. et al., *J. Clin. Invest*, 60:171–180 (1977)) is another technique in which antibody can be used after labeling with a radioactive isotope such as $^{125}$I. Some of these immunoassays can be easily automated by the use of appropriate instruments such as the IMx™ (Abbott, Irving, Tex.) for a fluorescent immunoassay and Ciba Coming ACS 180™ (Ciba Corning, Medfield, Mass.) for a chemiluminescent immunoassay.

Immunoprecipitation

Immunoprecipitation is another means of identifying small amounts of protein in a complex mixture by its interaction with antibody. The amount of antigen present can be determined by changes in turbidity of a solution using optical detection means such as a spectrophotometer, or the precipitate isolated and measured by detection of label on the antibody, typically using ELISA, measurement of a fluorescent label or measurement of a radiolabel. In those cases where the antibody does not precipitate antigen, precipitation may be enhanced through the use of a second anti-antibody or a second antibody immunoreactive with the same antigen.

For example, in an immunoturbidimetric assay for LDL, one preferably would use a single monoclonal antibody capable of precipitating exclusivly LDL. Single Monoclonal antibodies generally do not precipitate the antigens they are immunoreactive with. Accordingly, two or more Monoclonal antibodies immunoreactive with the same antigen can be used to precipitate the antigen. For quantitation of LDL, one would use two monoclonal antibodies which are specific for LDL. Useful antibodies include HB3cB3 combined with another antibody such as WbA53aC1-A6, described by Koren, et al. *Biochemistry* 26, 2734–2740 (1987). This results in immunoprecipitation of LDL without affecting other plasma lipoproteins such as VLDL and HDL.

In addition, the above-described sandwich method can be used to detect any blood protein of interest in a particular sample, provided, as described above, that either two distinct Monoclonal antibodies are available which do not interfere with each other's binding to the particular protein, or one MAb and a polyclonal antibody are available for the particular protein and the MAb is allowed to bind to the particular protein before the polyclonal antibody.

As noted above, anti-LDL Monoclonal antibodies, such as $HB_3cB_3$, are useful for quantification of LDL-cholesterol in antibody-antigen precipitation techniques and enzyme-linked immunosorbent assays (ELISA). For example, in a precipitation method the anti-LDL MAb is added to human serum or plasma and allowed to bind to LDL. The immune complex of LDL bound to anti-LDL MAb is then precipitated by mixing in an excess amount of protein A or an anti-mouse IgG polyclonal antibody. Precipitation of the complexes is enhanced by centrifuging the mixture and then discarding the supernatant. The precipitate containing LDL is then washed and dissolved in 8 M urea in PBS or treated with detergents such as Triton X-100 and cholic acid (Sigma, St. Louis, Mo.). This is followed by determination of LDL-cholesterol using an enzymatic assay for cholesterol (Sigma, St. Louis, Mo.).

Antibodies can be bound to a solid phase material for use in assays described herein. Various types of adsorptive materials, such as nitrocellulose, Immobilon™, polyvinyldiene difluoride (all from BioRad, Hercules, Calif.) can be used as a solid phase material to bind the anti-lipoprotein antibodies. Other solid phase materials, including resins and well-plates or other materials made of polystyrene, polypropylene or other synthetic polymeric materials can also be used. In the preferred embodiment for assaying lipoprotein concentrations, pieces or strips of these materials are coated with one or more antibodies, or functional fragments thereof, directed against specific epitopes of HDL, LDL, other lipoproteins, or apolipoproteins for use in patient samples. Such strips are referred to herein as "dipsticks". The dipsticks may also be attached to one end of a longer strip of a solid support material, such as plastic, which can serve as a handle for dipping a dipstick into a solution or sample. The plastic handle can also serve as a tether so that multiple dipsticks can be attached to a common support. Such a multi-strip design may be particularly useful in a set-up for testing multiple lipoproteins and/or apolipoproteins simultaneously.

Although various sizes of dipsticks are possible, typically, pieces of the solid phase material that are coated with antibody have the general dimensions of 0.5 cm×0.5 cm and can be attached to the longer solid support strips having general dimensions of 0.5 cm×5 cm. Such dimensions permit an accurate determination of lipoprotein or apolipoprotein levels in as little as 100 µl of sample.

The present invention will be further understood by reference to the following non-limiting examples.

EXAMPLE 1

Demonstration of the Presence of Apolipoproteins in Saliva

A. Polyacrylamide gel electrophoresis

Sample preparation

Fresh saliva samples were collected into test tubes and analyzed within 30 minutes or were kept overnight at 4C with 0.1% sodium azide. Serum samples were used as molecular weight markers; these were kept frozen and were thawed before analysis. Lipoproteins, HDL and LDL and apolipoproteins, ApoAI and ApoB from human plasma were from Calbiochem, La Jolla, Calif. Before electrophoresis all samples were treated with 2.5% sodium dodecyl sulfate (SDS) and incubated for 5 minutes in boiling water bath. In another variation of above treatment, the incubation mixture contained also 1% dithiothreitol (DTT). Bromophenol blue indicator was added to samples prior to electrophoresis.

Electrophoresis

Electrophoresis was performed with Phast System (Pharnacia Biotech, Piscataway, N.J.) using manufacturers' protocols and materials. The polyacrylamnide gel at a pH 4–15 gradient and buffer system consisted of 0.2 M Tris buffer, pH 8.1 with 0.55% SDS. Pretreated samples were applied to gels and gels were subjected to automated separation according to the protocol provided by Pharnacia. After completion of electrophoresis, gels were stained with Coomassie Blue R-350 and then destained and analyzed.

Results

Results from electrophoresis of unreduced samples were as follows: The HDL sample and ApoAI sample migrated as single bands. Relative mobility (Rf), measured with reference to bromophenol blue marker was 0.94 for each one. Rf for LDL sample was 0.24 and for ApoB sample was 0.25. The serum sample showed three bands at the region relative to HDL (Rf were 0.97; 0.94; and 0.88) and one band at the region relative to LDL (Rf0.24). Saliva samples showed two bands at the region relative to HDL (Rf were 0.94 and 0.91) and one band at the region relative to LDL (Rf=0.24-in one case Rf=0.22).

Electrophoresis for DTT reduced samples showed HDL and ApoAI as single bands with Rf=0.85 for each. LDL appeared as two bands (Rf0.26 and 0.22) and ApoB was a single band (Rf=0.26). Serum sample showed two bands at the region relative to HDL (Rf0.82 and 0.79) and no sharp bank in LDL area. Saliva samples showed a single band at the region relative to HDL (Rf=0.82 for each saliva sample) and no sharp band at the region relative to LDL.

Protein bands were only visible on gels when freshly collected saliva samples were analyzed.

B. Western Blotting.

Protein Blotting

Protein blotting was done essentially according to the Phast System™ Development Technique File 220: Nitrocellulose (supplied with the Phast System unit) was prewetted with 1×PBS. Upon completion of electrophoresis the nitrocellulose was placed on top of the gradient gel and the temperature was increased to 70° C. and diffusion-mediated transfer proceeded for 20–30 minutes.

The nitrocellulose was incubated with shaking for 1 hour at RT followed by washing for 5 minutes in wash buffer (WB, 1×PBS, 0.05% TWEEN®20). The blot was then incubated with shaking for 30–60 minutes with a 1:1000 dilution of mouse anti-apolipoprotein B (monoclonal $W_aB_2bD_6$, immunoreactive with ApoB independent of lipid content, obtained from Dr. Eugen Koren, Oklahoma Medical Research Foundation, Oklahoma City, Okla.) in 10 mg/ml BSA, 1×PBS. After a 5 minute wash in WB the gel was incubated for 30–60 minutes at room temperature (RT) with shaking with a 1:500,000 dilution of horseradish peroxidase (HRP) goat anti-mouse conjugate (Jackson InmunoResearch; West Grove, Pa.) and subsequently washed 6 times. The blot was submerged in chemiluminescent development reagent SUPERSIGNAL BLAST™(Pierce; Rockford, Ill.) for five minutes, placed in a transparent laminate, exposed to BIOMAX™ MR-2 film (Kodak; Rochester, N.Y. for 10 seconds and developed with KODAK™ developer and fixer as per manufacturer's instructions.

Results

Monoclonal anti-apolipoprotein B stained material of very high molecular weight was observed for both purified Apolipoprotein B and purified LDL. Each of these sample showed a faint band at the approximately 60 kd site. In saliva the predominant staining was seen at approximately 60 kd mw. When Apolipoprotein B was added to the saliva sample and incubated for 1 hour at room temperature prior to electrophoresis, a decrease in the amount of the high molecular weight band and a distinct increase in the immunoreactive material at approximately 60 kd mw was observed, indicating that Apo B is degraded by the saliva enzymes.

Serum samples generated three bands that reacted with anti-Apo B, a double band at very high molecular weight which was also seen in purified LDL, and an approximately 60 kd and possibly 45 kd mw fraction. Purified LDL showed only a very high molecular weight band. Apo A1 was present in saliva in the 30 kd serum form. Apo B immunoreactive with antibody was present in an approximately 60 kd form: When LDL or ApoB was added to saliva and incubated the same approximately 60 kd immunoreactive form was generated, indicating that the degradation is by saliva enzymes.

The levels of ApoA1 and ApoB measured in saliva by Western blot corresponded to about $1/50^{th}$ of the amount seen in serum.

EXAMPLE 2

Correlation of ApoA:ApoB Saliva Levels with ApoA:ApoB Serum Levels.

Sample Collection

Saliva: Stimulated and unstimulated saliva was collected and analyzed. Saliva flow was stimulated by asking the individual to suck either a lemon or a super mint. Stimulated saliva was collected by stimulating the same individual five minutes after collection of unstimulated saliva. Saliva samples were immediately filtered through a serum separator and then chilled in an ice water bath. Saliva samples were assayed within three hours of collection.

Stimulated saliva provided superior correlation. The super mint gave superior results and was more acceptable to saliva donors.

Serum: Serum was collected from 12 fasting subjects, immediately frozen and was thawed immediately before testing.

Analysis of Serum Lipids

Serum samples were analyzed for serum lipids on the Roche Cobas Mira Automated Chemistry Analyzer (software version 8735; Roche Diagnostic System, Nutley, N.J.). Roche Apo A-1 and Apo B reagents and apolipoprotein standards were used to set up the calibration curve for determination of Apo A-1 and B in both serum and saliva samples. Roche cholesterol reagent and calibrator serum were used to determine the level of total cholesterol. Roche Unimate HDL direct HDL-Cholesterol calibrator and HDL direct calibrator were used to determine the level of HDL cholesterol. Roche triglycerides reagent and calibrator were used to determine the level of VLDL cholesterol, which is one-fifth of triglycerides. LDL cholesterol was determined as the difference of the determined sum of the VLDL and HDL cholesterol from total cholesterol.

For each of the assays, assay accuracy was monitored by comparison of experimental values to the published values for Liquichek and Lyphochek control levels I and II (Bio-Rad; Hercules, Calif.) and for Cardiolipid and Apolipoprotein control levels I and II (Sigma Diagnostics; St. Louis, Mo.). Assay precision was estimated by determining average %CV of the same samples on successive days using Roche Reagents and additionally assayed for ApoA1 and ApoB by Elisa Immunoassay of Lipoproteins. The correlation of the Roche serum assay with the Elisa was used to demonstrate correlation of the assays.

ELISA for Apo A-1 and B in Saliva:

Microtiter plates were coated overnight at RT and 100 microliters per well of Apo A-1 or B from Intracell, Issaquah, WA added. Wells were blocked with 1% BSA/PBS for 2 hrs at RT. 10 microliters of saliva sample was incubated for 15 minutes at RT with 90 microliters of either rabbit polyclonal anti ApoA-1 (antibody provided by E. Koren, San Francisco) at 1:30,000 dilution or a 1:25,000 dilution of goat polyclonal anti ApoB (also provided by E. Koren, OMRF). After a thirty minute incubation RT, plates were washed twice with 0.1% BSA/PBS. 100 microliters of HRP goat anti rabbit (ApoA-1 determination) or HRP rabbit anti-goat (ApoB determination) (Jackson InmuunoResearch was added with shaking at RT for 30 minutes). This was followed by two washes with BSA/PBS and followed by the addition of 150 microliters of 3, 3', 5, 5' tetramethyl-benzidine (TMB) for 15 minutes with shaking. The colorimeteric reaction was stopped with 2 N sulfuric acid and plates were read on a Titertek Plate Reader at 450 nm to determine final absorbance. Absorbance readings were converted to mg/dL of ApoA-1 and B by reference to a calibration curve for ApoA-1 and B constructed from different dilutions of a serum sample pool. ApoA-1 and B values for the undiluted sample pool were determined from the Roche autoanalyzer assay.

Elisa for Albumin

Microtiter plates were coated overnight at RT with 100 microliters per well of human serum albumin (Sigma A1151, St. Louis, Mo.) at 2 microgram/ml. Wells were blocked with 1% BSA/PBS for 2 hrs at RT. 10 microliters of saliva at 1:10 and 10 microliters at 1:100 was preincubated for 15 minute at RT with 90 microliters of goat anti-human albumin A1:100K and then transferred to the plate. After a thirty minutes incubation at RT, plates were washed twice with 0.1% BSA/PBS. 100 microliters of HRP rabbit anti-goat (Jackson ImmunoResearch) was added with shaking at RT for 30 minutes. This was followed by two washes with BSA/PBS and followed by the addition of 150 ul of 3, 3'5, 5' tetramethyl-benzidine (TMB) for 15 minutes with shaking. The colorimeteric reaction was stopped with 2N suliric acid and plates were read on a Titertek Plate Reader at 450 nm to determine final absorbance. Absorbance readings were converted to mg/dL of albumin by reference to a calibration curve constructed from different dilutions of a Sigma Human serum albumin.

Results

Figure 1:
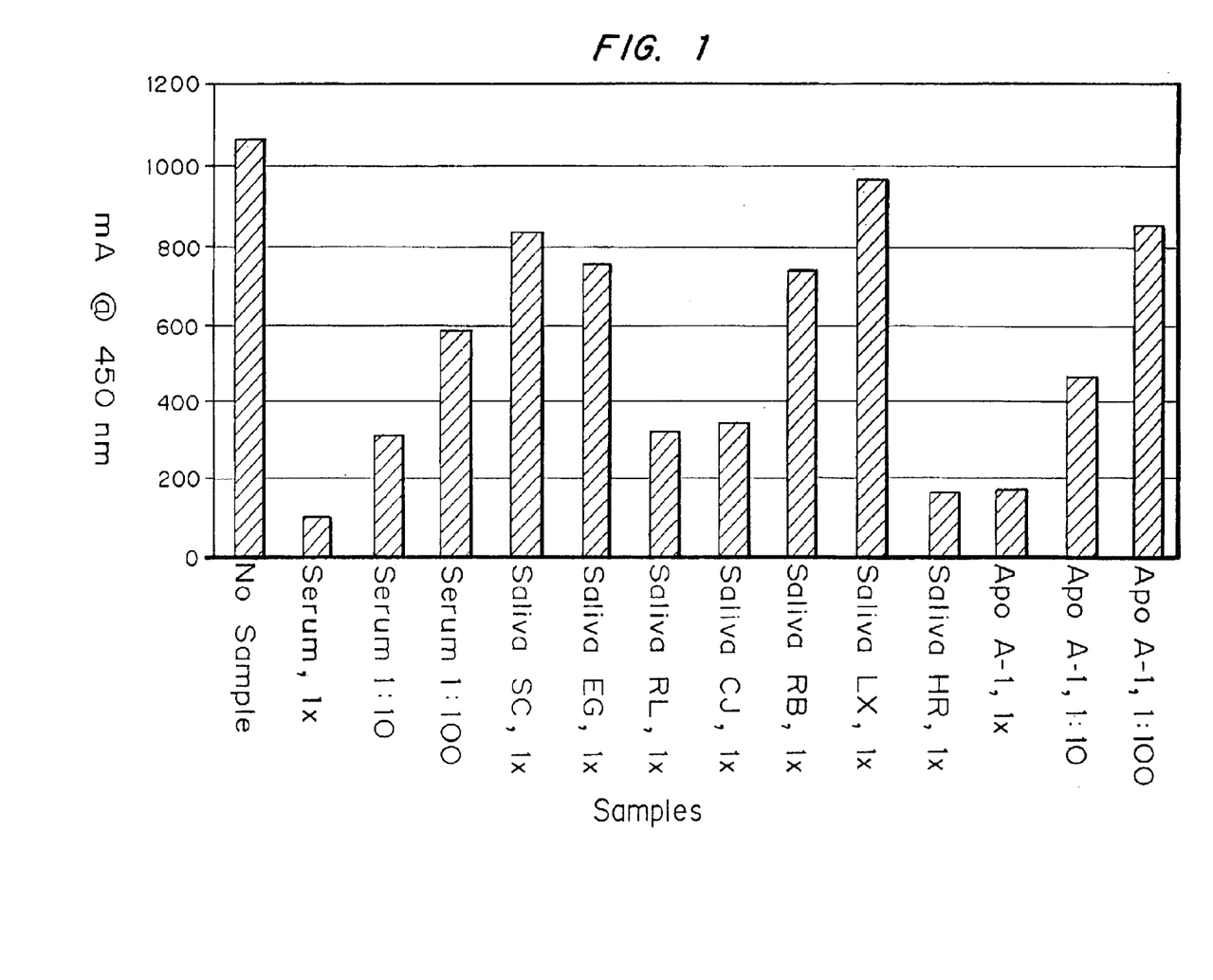
FIG. 1 is a graph of the absorbance of saliva samples assayed by ELISA for the presence of HDL, using serum and Apo A1 at different dilutions (1×1:10, 1:100) as controls.

Lipoproteins in serum and saliva samples competed with lipoproteins coated on plates for anti-apolipoprotein antibody binding, as shown by FIG. 1. With increasing amount of lipoprotein in the sample, less antibody bound to the plate and decrease in signal was observed. Seven saliva samples exhibited different levels of measured apolipoproteins. The level of Apo A1 measured by ELISA in saliva samples was less than 10% of the expected serum level of Apo A1. The level of ApoB measured by ELISA in saliva samples was less than 1% of the serum level of Apo B.

The correlation between the values measured in serum samples using the commercially available Roche assay and the ELISA for Apo A and Apo B is shown in Table 1. The correlation between the values measured in serum samples for Apo A1 and Apo B by the Roche assay and serum LDL and HDL measured by the ELISA is shown in Table 2.

The correlation between Saliva Apo B/A1 and Serum Apo B/A1, measured by ELISA is shown in Table 3. In stimulated saliva samples, albumin is secreted in the same manner as the Apo B. As a result, albumin can be used to correct for dilution of the saliva sample. Apo B levels in saliva and Apo B levels normalized for dilution by reference to albumin correlate highly with serum Apo B and LDL levels.

Figure 2A:
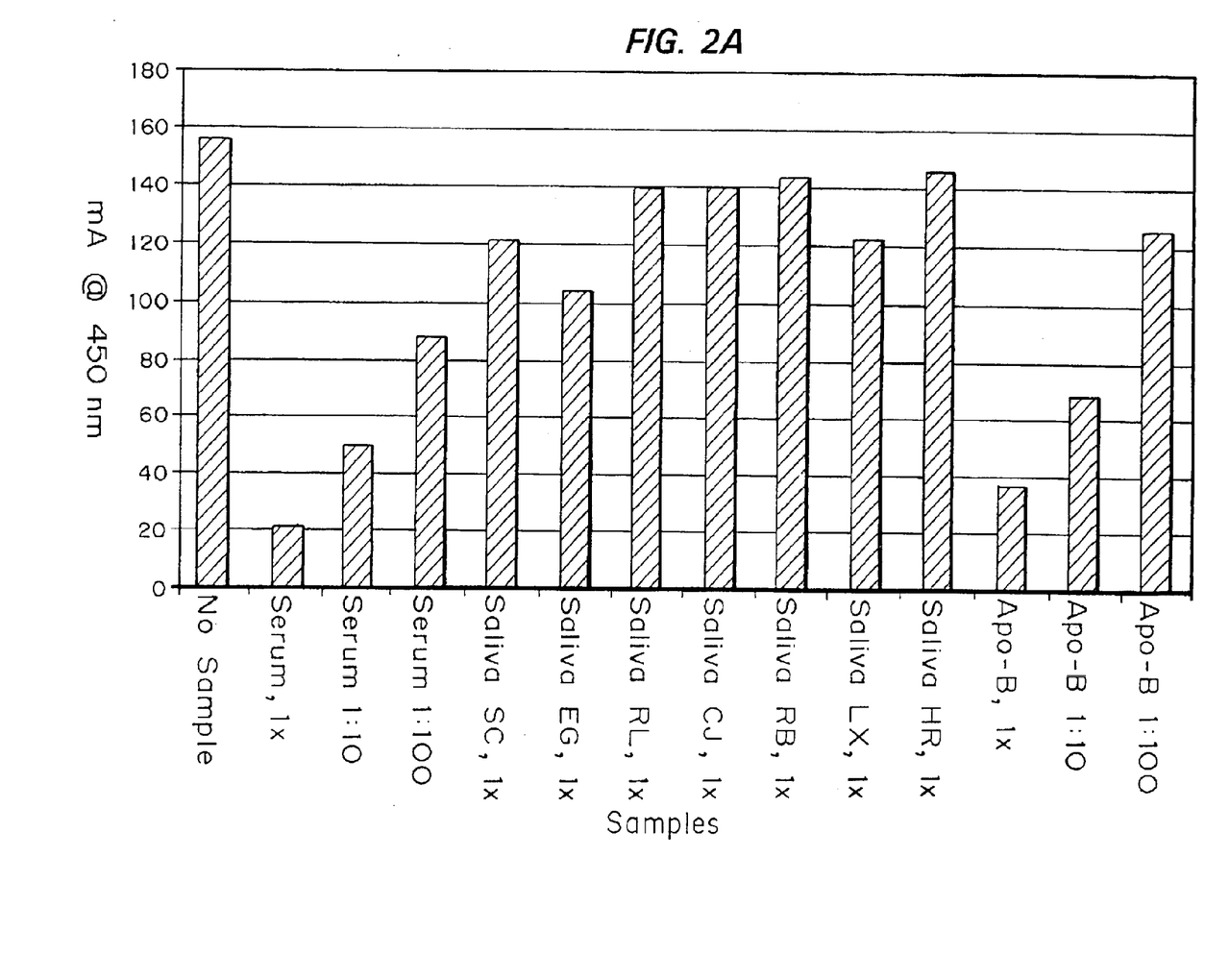
FIG. 2A is a graph of the absorbance of saliva samples assayed by ELISA for the presence of LDL, using serum and Apo B as different dilutions (1×, 1:10, and 1:100) as controls.
Figure 2B:
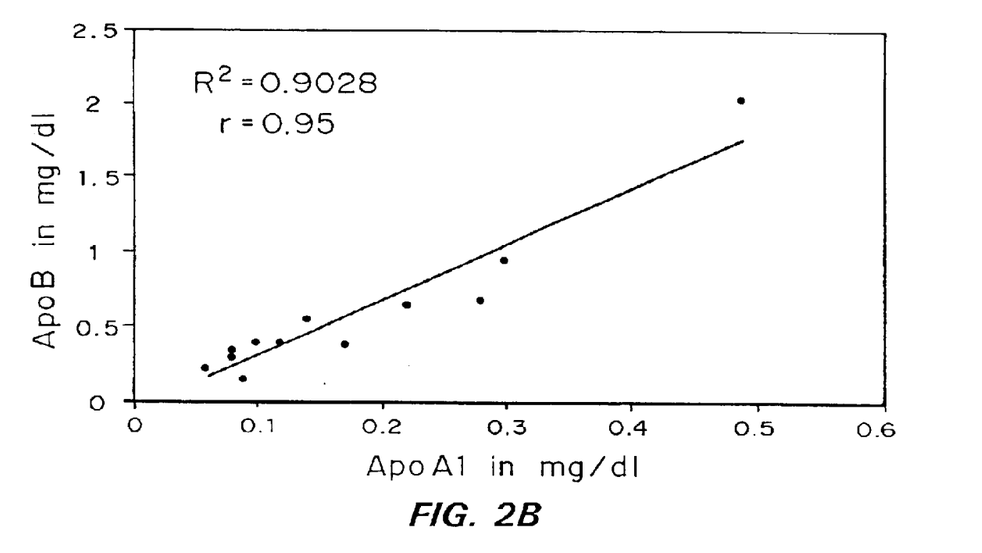
FIG. 2B is a graph of Apo B (mg/dl) relative to Apo A1 (mg/dl) in lemon stimulated saliva.
Figure 2C:
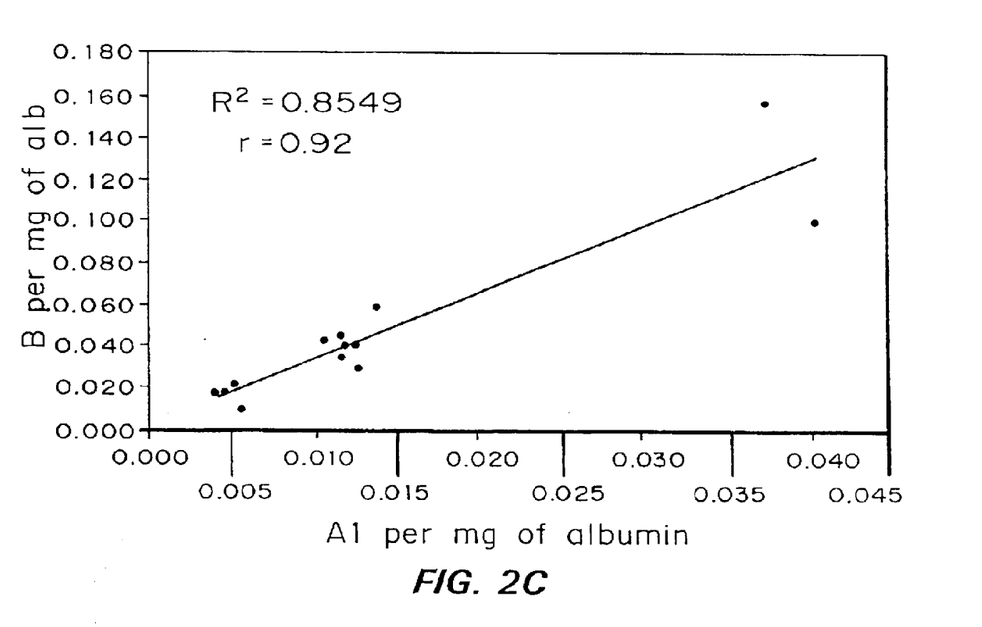
FIG. 2C is a graph of Apo B (mg/dl) relative to Apo a1 per mg of albumin in lemon stimulated saliva.

The correlation coefficient for the Apo A:Apo B ratio obtained with stimulated saliva is not as high as the correlation coefficient in unstimulated salivastimulated saliva's when expressed in a Apo A/Apo B ratio did not correlate as well as unstimulated saliva. Apo A lipoprotein levels correlate highly r=0.95 and 0.92 with Apo B levels whether expressed as mg/dL or normalized to saliva albumin FIGS. 1a and b. In contrast the serum ApoA:B levels for these same samples had r=less than 0.04. Thus it appears that during stimulated and (unstimulated) saliva flow Apo B secretion increases in relation to the amount of ApoA-1 and is on the order of three to four times as much Apo B as Apo A, as shown in FIGS. 2B and 2C in contrast to the serum Apo B/Apo A ratio, which ranges from 0.36 to 1.4. Thus, there is much higher Apo B:Apo A ratio than observed in serum. This could reflect the selectively higher secretion of Apo B in saliva or may be an artifact reflecting that the partially fragmented Apo B is more immunoreactive than the intact B protein.

TABLE 1

Correlation (r) of the Roche Serum Assays with the Serum ELISA for Apo A and Apo B.

| Roche Values | ELISA Apo A1 | ELISA Apo B | ELISA Apo B/A1 |
|---|---|---|---|
| ApoA1 | 0.81 | | |
| ApoB | | 0.94 | |
| ApoB/A1 | | | 0.93 |

TABLE 2

Correlation (r) of Roche Serum Apo A1 and Apo B with Serum LDL and HDL Measured by ELISA.

| | LDL | HDL | LDL/HDL |
|---|---|---|---|
| ApoA1 | | 0.95 | |
| ApoB1 | 0.98 | | |
| ApoB/A1 | | | 0.99 |

TABLE 3

Correlation (r) of Saliva ApoB/A1 with Serum ApoB/A1 Measured by ELISA.

| Saliva | Serum ApoB/A1 | Serum ApoB | Serum LDL |
|---|---|---|---|
| ApoB/A1 | 0.75 | | |
| ApoB/Albumin | | .88 | .82 |

EXAMPLE 3

Detection of Saliva Levels of ApoB and ApoA-1 in Competitive Format Immunochromatographic Strips.

Preparation of Immunochromatographic Strips 5 micron Nitrocellulose membrane (Millipore, Burlington, Mass.) was coated with human HDL or LDL from Calbiochem, La Jolla, Calif. at a concentration of 2 mg/ml in an amount of 3 microliters/3 mm wide strip using a Camag Linomat IV (CAMAG, Switzerland). Gold particles were coated with anti-ApoA1 with the monoclonal Lpa1HB4 (American Type Culture Collection, Rockville, Md.), or with anti-ApoB with WaB2bD6 (Dr. Koren, OMRF).

Preparation of Samples

To assay, serum samples were diluted 1:2000, 1:600, 1:100, 1:75, 1:25 and 1:10 50 into PBS. 50 microliter of sample was pipetted into a test tube containing 5 microliters of gold conjugate and 5 microliter of 5% BSA (Sigma, St. Louis, Mich.). The sample was vortexed and a strip was inserted in the tube. When the fluid had migrated to the end of the strip, the strip was removed from the tube, allowed to dry and the intensity of the band was measured using a Graytag D19C/D196 remission Densitometer (Greytag, Switzerland).

Results

Figure 3A:
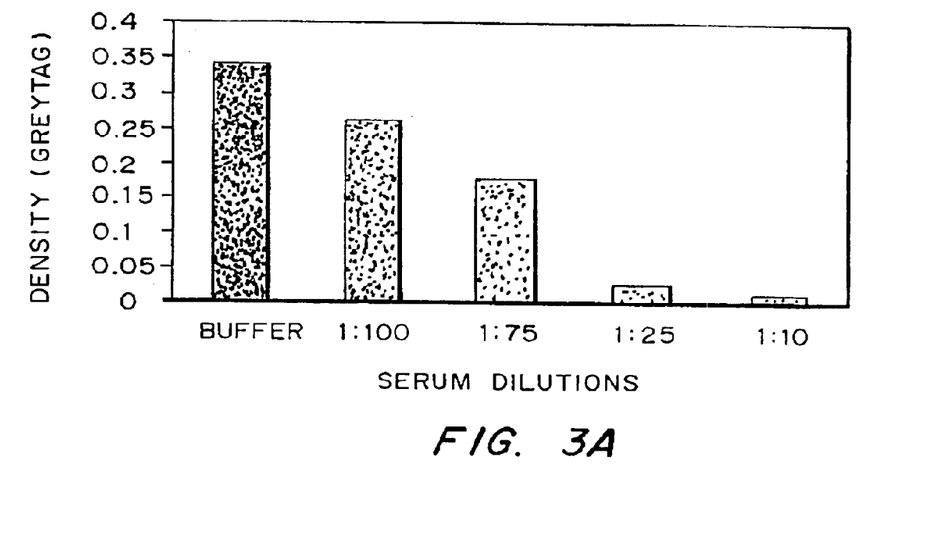
FIG. 3a is a graph of color density in a strip immunoassay for LDL for LDL in serum at dilutions of 1:100, 1:75, 1:25 and 1:10.
Figure 3B:
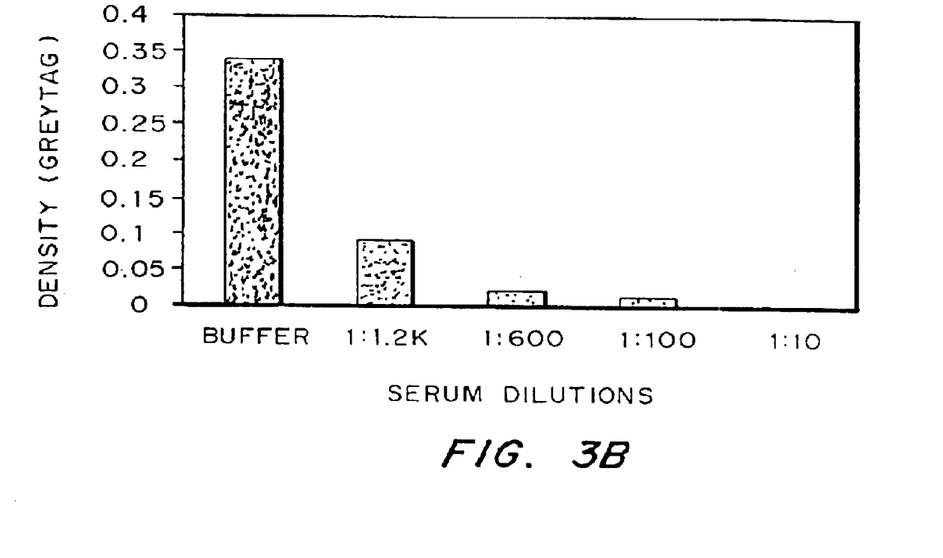
FIG. 3b is a graph of color density in a strip immunoassay for HDL for HDL in serum at dilutions of 1:1,200, 1:600, 1:100, and 1:10.
Figure 4A:
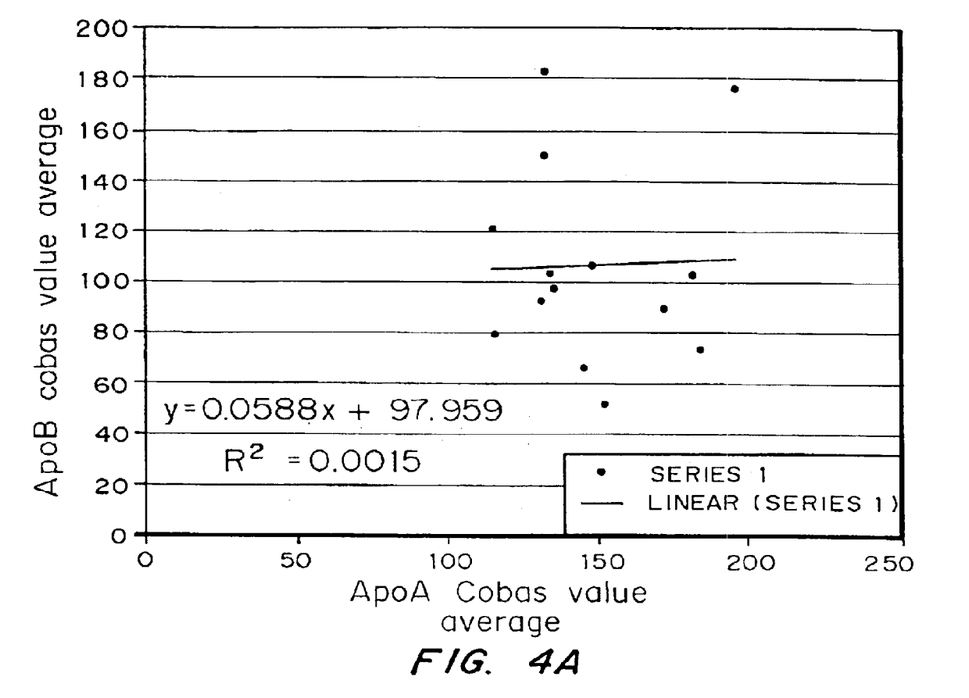
FIG. 4a is a graph of the correlation of the rato of Apo B to Apo A in serum.
Figure 4B:
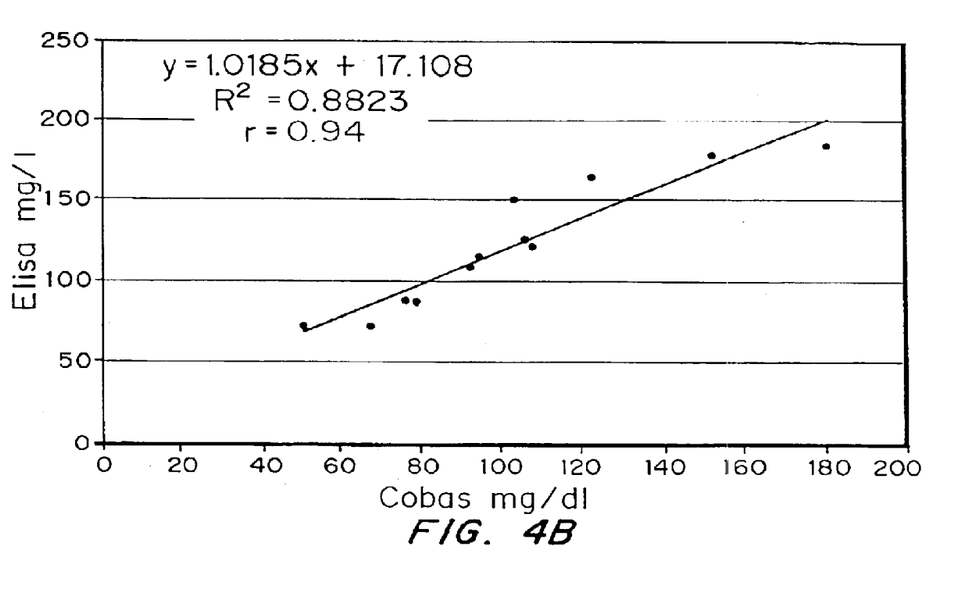
FIG. 4b is a graph of the correlation of the ratio of Apo B in serum measure by the ELISA described herein compared to the Roche commercially available Cobas Mira assay.
Figure 4C:
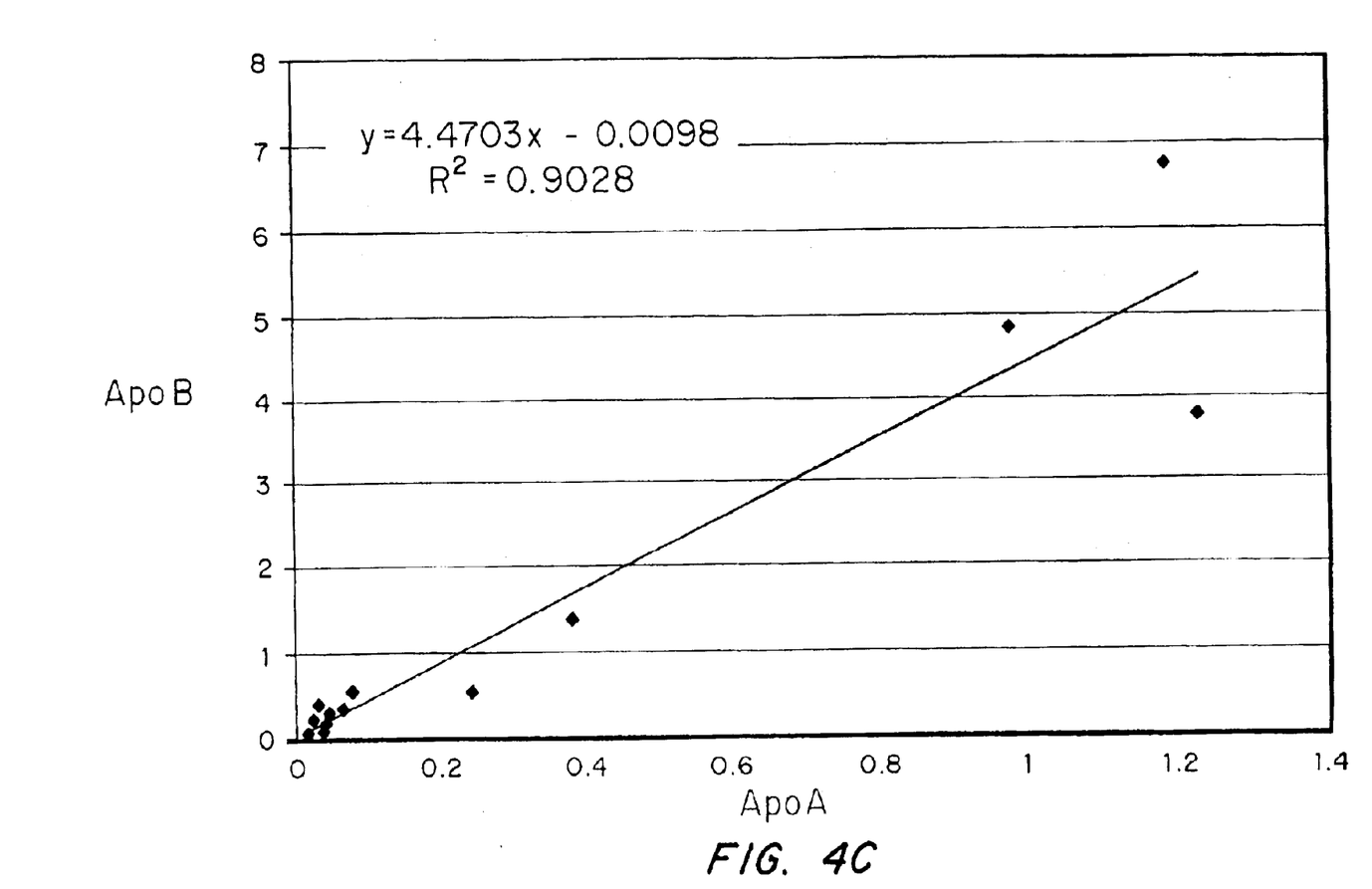
FIG. 4c is a graph of the correlation of the ratio of Apo B to Apo A in lemon stimulated saliva

FIG. 3a and FIG. 3b shows that color intensity was strongly inhibited by a 1:2000 dilution of serum and 1:100 dilution of Apo B. There was a good dose dependent inhibition of binding. Since saliva has an average of $1:50^{th}$ of the amount of Apo A1 and at least that amount of ApoB, the results demonstrate that the assay of Apo A1 and Apo B in saliva proteins is amenable to quantitative immunochromatographic detection and could be adapted to the Serex reland format described in U.S. Pat. Nos. 5,451,504, 5,500, 375, and 5,710,00.

Modifications and variations of the methods and materials described herein will be obvious to those skilled in the art and are intended to come within the scope of the appended claims.

What is claimed is:

1. A method for determining the level of an apolipoprotein in the serum of an individual based on levels of the apolipoprotein in the individual's saliva comprising
   obtaining a saliva sample from an individual,
   reacting the apolipoproteins in the saliva sample with antibodies immunoreactive with one or more of the apolipoproteins, wherein the antibodies are in a quantitative assay which measures the amount or concentration of bound complexes between apolipoproteins and the antibodies immunoreactive therewith,
   determining the amount of apolipoproteins in the serum of the individual by comparing the immunoreactive between the antibodies and apolipoproteins in the saliva sample by reference to standards of known amounts of apolipoproteins in saliva and serum.

2. The method of claim 1 wherein the apolipoprotein is selected from the group consisting of Apo A, Apo B, Apo C, and Apo E.

3. The method of claim 2 wherein the apolipoprotein is selected from the group consisting of Apo A1 and Apo B.

4. The method of claim 1 wherein the antibodies are labeled with a detectable label.

5. The method of claim 1 further comprising determining the level of apolipoprotein in the saliva sample within less than three hours following collection.

6. The method of claim 1 further comprising preparing the saliva in the sample by removing mucopolysaccharides from the saliva prior to determining the level of apolipoprotein in the saliva sample.

7. The method of claim 1 further comprising collecting the saliva after stimulating its secretion from a subject.

8. The method of claim 1 further comprising determining the amount of albumin present in the saliva.

9. The method of claim 8 further comprising correcting the determined amount of the apolipoprotein for the presence of albumin in the saliva sample.

10. The method of claim 1 wherein the saliva sample is collected into a device which filters out mucopolysaccharides and which comprises the antibodies immunoreactive with one or more of the apolipoproteins in the saliva sample.

11. The method of claim 10 wherein the apolipoprotein is either Apo A1 or Apo B.

12. An assay device or kit for determining the amount of apolipoprotein in a saliva sample comprising means for collection of saliva, antibodies immunoreactive with one or more apolipoproteins, wherein the antibodies are in a quantitative assay which measures the amount or concentration of bound complexes between apolipoproteins and the antibodies immunoreactive therewith, and standards of known amounts of apolipoproteins in saliva and serum.

13. The assay device or kit of claim 12 comprising filter means for removal of mucopolysaccharides from the saliva.

14. The assay device or kit of claim 12 wherein the antibodies are reactive with apolipoprotein selected from the group consisting of Apo A, Apo B, Apo C, and Apo E.

15. The assay device or kit of claim 12 further comprising antibodies immunoreactive with albumin.

16. The assay device or kit of claim 12 wherein the antibodies immunoreactive with apolipoprotein in the saliva sample are immobilized on a solid support.

17. The assay device or kit of claim 16 comprising reagents for detection of complexes between the apolipoprotein and the antibodies.

18. The assay device or kit of claim 12 comprising a strip or dipstick.

19. The assay device or kit of claim 15 comprising a first reagent consisting of antibodies to the apolipoprotein and a second reagent consisting antibodies to albumin.

20. A method for quantitating the amount of lipoprotein or cholesterol in saliva or determining the risk of cardiovascular disease from a saliva sample comprising obtaining a saliva sample from an individual, reacting the apolipoproteins in the saliva sample with antibodies immunoreactive with one or more of the apolipoproteins, wherein the antibodies are in a quantitative assay which measures the amount or concentration of bound complexes between apolipoproteins and the antibodies immunoreactive therewith, determining the amount of apolipoproteins in the serum of the individual by comparing the immunoreactivity between the antibodies and apolipoproteins in the saliva sample by reference to standards of known amounts of apolipoproteins in saliva and serum from normal or at risk individuals.

21. The method of claim 1 further comprising, correlating the levels of one or more lipoproteins selected from the group consisting of high density lipoprotein and low density lipoprotein, in the serum with the levels of apolipoprotein subtypes in the serum, correlating the levels of the apolipoprotein subtypes in the serum based on the levels of apolipoprotein subtypes determined in the saliva sample, and extrapolating the levels of the lipoprotein in the serum, based on the levels of the apolipoprotein subtypes determined in the saliva sample.

22. The method of claim 20 comprising reacting the apolipoprotein in the saliva sample with antibodies specifically immunoreactive wit an apolipoprotein selected from the group consisting of Apo A, Apo B, Apo C, and Apo E, and correlating the levels of at least one apolipoprotein in the saliva with the levels of apolipoprotein in serum samples of patients having lipid disorders or risk of cardiovascular disease.

* * * * *

UNITED STATES PATENT AND TRADEMARK OFFICE
CERTIFICATE OF CORRECTION

PATENT NO. : 6,808,889 B2 Page 1 of 1
APPLICATION NO. : 09/526582
DATED : October 26, 2004
INVENTOR(S) : Judith Fitzpatrick, Regina B. Lenda and Christopher L. Jones It is certified that error appears in the above-identified patent and that said Letters Patent is hereby corrected as shown below:

Column 14:
Claim 1, line 39, replace "immunoreactive" with --immunoreactivity--.

Signed and Sealed this

Thirty-first Day of July, 2007

JON W. DUDAS
*Director of the United States Patent and Trademark Office*